United States Patent [19]
Mardente et al.

[11] Patent Number: 6,149,893
[45] Date of Patent: Nov. 21, 2000

[54] PHARMACEUTICAL COMPOSITIONS CONTAINING CALCITONIN IN A SPRAY DOSING FEEDER FOR INTRANASAL ADMINISTRATION

[75] Inventors: Salvatore Mardente, Turin; Leone Gabriele Rotini, Bologna, both of Italy

[73] Assignee: Alfa Wassermann S.p.A., Alanno Scalo, Italy

[21] Appl. No.: 09/259,728

[22] Filed: Mar. 1, 1999

[51] Int. Cl.[7] ........................................ A61K 9/12
[52] U.S. Cl. ............................ 424/45; 424/434
[58] Field of Search ........................ 424/45, 434

[56] References Cited

U.S. PATENT DOCUMENTS 5,514,365  5/1996  Mardente et al. ..................... 424/45
5,756,071  5/1998  Mattern et al. ....................... 424/45
5,792,469  8/1998  Tipton et al. ......................... 424/422

OTHER PUBLICATIONS

Gomori, G. Preparation of buffers for use in enzyme studies in Methods in Enzymology, vol. 1, 1955. S.P. Colowick and N.O. Kaplan eds. Academic Press, N.Y. pp. 138–146.

*Primary Examiner*—Thurman K. Page
*Attorney, Agent, or Firm*—Bucknam and Archer

[57] ABSTRACT

Pharmaceutical compositions for intranasal administration containing in a spray dosing feeder calcitonin dissolved in a substantially physiological solution of sodium chloride adjusted to a pH between 3.5 and 4.5 with citrate buffer and hydrochloric acid without any preservative are the object of the present invention.

4 Claims, No Drawings

PHARMACEUTICAL COMPOSITIONS CONTAINING CALCITONIN IN A SPRAY DOSING FEEDER FOR INTRANASAL ADMINISTRATION

DESCRIPTION OF THE INVENTION

The present invention relates to pharmaceutical compositions for intranasal administration containing in a spray dosing feeder calcitonin, preferably salmon calcitonin also known under the denomination of salcatonin, dissolved in a substantially physiological solution of sodium chloride adjusted to a pH between 3.5 and 4.5 with citrate buffer and hydrochloric acid and free from any preservative.

The therapeutical action carried out by the calcitonin in the treatment of osteoporosis, Paget's disease and hypercalcemia is known.

It is also known how the various calcitonins, having polypeptidic structure, are easily deteriorated and cannot be administered by oral route, while the administration by parenteral route shows many drawbacks including also painful reactions.

Many drugs of peptidic nature are administered by intranasal route in order to avoid the above mentioned drawbacks, as it is described, for instance, from Felber et al., Experientia, 1969, page 1195, from Gennser et al., Lancet, 1974, page 865 and from Greenberg et al., Antimicrobial Agents and Chemotherapy, 1978, page 596.

Many patent documents describe and claim pharmaceutical compositions for the intranasal administration of calcitonin.

Italian patent 1172324 claims pharmaceutical compositions containing calcitonin, benzalkonium chloride and/or a surfactant.

These additives are stated to be necessary in order to guarantee a good bioavailability of the calcitonin, i.e. in order to warrant its effective absorption from the nasal mucosa, and the benzalkonium chloride is stated to be necessary as preservative against pathogenic microorganisms. European patent EP 193372 claims analogous compositions containing a quaternary ammonium salt like benzalkonium chloride and cetyltrimethylammonium bromide both as preservative and absorption accelerators.

U.S. Pat. No. 5,514,365 claims a method of treatment of a patient suffering from any of osteoporosis, Paget's disease and hypercalcemia by the intranasal administration by spray of a liquid composition containing calcitonin dissolved in an aqueous chloride solution free of quaternary ammonium compounds.

Many other patent documents claim nasal compositions of calcitonin containing absorption-increasing agents: Japanese patent application 61126034 claims the use of glucose and/or glucosamine, Japanese patent application 61118325 claims the use of aminoacids, lastly European patent EP 0183525 claims the use of benzyl alcohol, ethyl alcohol, salicylic acid and polyethylene glycol as absorption promoters.

The patent literature is therefore unanimous in underlining the need of adding additives of various kind to the intranasal compositions of calcitonin with the aim of keeping their preservation and of increasing their bioavailability.

Therefore it is really surprising the finding that pharmaceutical compositions for the intranasal administration containing in a spray dosing feeder calcitonin in a substantially physiological aqueous solution of sodium chloride adjusted to a pH between 3.5 and 4.5 with citrate buffer and hydrochloric acid possess the same bioavailability and preservation as the pharmaceutical compositions of calcitonin containing preservatives and/or absorption-increasing agents.

Pharmaceutical compositions for the intranasal administration containing in a spray dosing feeder therapeutically effective amounts of calcitonin dissolved in a substantially physiological solution of sodium chloride in purified water adjusted to a pH between 3.5 to 4.5 with citrate buffer and hydrochloride acid are the object of the present invention.

The citrate buffer is used to give a better stability of the pH of the solution during the period of validity of the product.

It is made by a mixture of citric acid monohydrate and of sodium citrate dihydrate, preferably the mixture is made by from 0.40 to 0.70 g of citric acid monohydrate and from 0.40 to 0.70 g of sodium citrate dihydrate for each liter of solution containing the calcitonin. The pH of the solution is adjusted to a value between 3.5 and 4.5 by adding a 1 N aqueous solution of hydrochloric acid, preferably between 0.08 g and 0.25 g for each liter of solution.

In a preferred aspect of the invention, the calcitonin used is salmon calcitonin, also known under the denomination of salcatonin, and the therapeutically effective amounts are between 500 and 2500 I.U. of calcitonin for each milliliter of solution.

In a further preferred aspect of the invention, the spray dosing feeder for the intranasal administration of the calcitonin is made by a bottle containing the solution of calcitonin and nitrogen under a pressure between 0.2 and 0.3 bar to whose mouth a dosing pump is fitted without valve of suction and delivery and equipped with a collar packing tightly fitting to the mouth of the bottle thereby providing a hermetic seal preventing any exchange of gas with the outside.

Said bottle can have a capacity between 5 and 10 ml and the dosing pump delivers about 100 microliters of solution at each working.

The pharmaceutical compositions according to the invention show the advantage, in comparison with those known from the prior art, to be free both of the quaternary ammonium salts whose undesired effects on the mucosas are known [*Am. J. Ophthalmol.,* 105, (6), 670–3, (1988); Contact Dermatitis, 17, (1), 41–2, (1987); Cutis, 39, (5), 381–3, (1987)] and of the other absorption-increasing agents which, even apart from possible undesired effects, anyway cause an increase of the manufacturing costs.

The examples hereinafter reported serve to further illustrate the pharmaceutical compositions object of the present invention and have not to be taken as an its limitation.

EXAMPLE 1

An amount of salcatonin corresponding to 1,000,000 I.U. is dissolved in a solution containing 8.7 g of analytically pure sodium chloride in 800 ml of purified water. The resulting solution is then added to 0.58 g of citric acid monohydrate, 0.58 g of sodium citrate dihydrate and 0.18 g of a 1 N aqueous solution of analytically pure hydrochloric acid.

The solution is adjusted to the volume of 1,000 ml of purified water, filtered on a 0.2 μm filter and shared into the spray dosing feeders calibrated for the administration of 0.1 ml of solution, equivalent to 100 I.U. of salcatonin, at each working.

EXAMPLE 2

Example 1 is repeated with the variations of using a double amount of salcatonin (2,000,000 I.U.). Each 0.1 ml dose corresponds to 200 I.U. of salcatonin.

EXAMPLE 3

Three batches of spray dosing feeders according to example 1 and three batches according to example 2 have been submitted to stability tests in a period of time between 3 and 18 months at a temperature comprised between +2° C. and +8° C. in a refrigerator.

Spray dosing feeders of each type have been tested before starting the stability test and then after 3, 6, 9, 12 and 18 months of storage in the refrigerator at a temperature between 2° C. and 8° C.

The following parameters have been tested: appearance, clarity, coloration, pH, salcatonin amount both through biological and HPLC methods, related substances and sterility.

The average values of all these parameters have shown to be practically unchanged along the whole period of time of the stability test as it is clearly illustrated in the following tables 1 to 6.

The quality specification fixed for the stability of the salcatonin solutions contained in the salcatonin solutions contained in the spray dosing feeders submitted to the stability tests are as follows:

| | |
|---|---|
| Appearance: | clear colourless solution |
| Clarity: | less than E.P. reference suspension I |
| Degree of coloration: | less than E.P. reference solution B9 |
| pH: | 3.5–4.5 |
| Salcatonin I.U./ml (Example 1): | 800–1250 |
| Salcatonin I.U./ml (Example 2): | 1600–2500 |
| Related substances: | individual ≦3% |
| Sterility: | sterile |

Batches 961080, 961090 and 961100 according to example 1 and batches 961110, 961120 and 961130 according to example 2 have been tested.

TABLE 1

Salcatonin stability - Batch 961080

| Tests | 0 Time | 3 Months | 6 Months | 9 Months | 12 Months | 18 Months |
|---|---|---|---|---|---|---|
| Appearance | Corresponds | Corresponds | Corresponds | Corresponds | Corresponds | Corresponds |
| Clarity | Corresponds | Corresponds | Corresponds | Corresponds | Corresponds | Corresponds |
| Degree of coloration | Corresponds | Corresponds | Corresponds | Corresponds | Corresponds | Corresponds |
| pH | 4.00 | N.D. | 4.08 | 4.01 | 4.09 | 4.20 |
| Salcatonin I.U./ml (biol.) | 1020 (969–1346)* | 1120 (1064–1489)* | 1100 (990–1474)* | 1060 (909–1410)* | 1010 (739–1426)* | 1030 (813–1393)* |
| Salcatonin I.U./ml (HPLC) | 1021 | 1023 | 1059 | 1022 | 981 | 936 |
| Related substances | Individual < 1% | Individual < 1% | Individual < 1% | Individual < 1% | Individual < 1% | Individual < 1% |
| Sterility | Sterile | N.D. | Sterile | N.D. | Sterile | N.D. |

*Confidence limits for error (P = 0.05)
N.D. = NOT DETERMINED

TABLE 2

Salcatonin stability - Batch 961090

| Tests | 0 Time | 3 Months | 6 Months | 9 Months | 12 Months | 18 Months |
|---|---|---|---|---|---|---|
| Appearance | Corresponds | Corresponds | Corresponds | Corresponds | Corresponds | Corresponds |
| Clarity | Corresponds | Corresponds | Corresponds | Corresponds | Corresponds | Corresponds |
| Degree of coloration | Corresponds | Corresponds | Corresponds | Corresponds | Corresponds | Corresponds |
| pH | 4.03 | 4.04 | 4.09 | 4.00 | 4.10 | 4.19 |
| Salcatonin I.U./ml (biol.) | 1070 (974–1358)* | 1090 (1014–1384)* | 1070 (867–1540)* | 1060 (931–1287)* | 1040 (921–1287)* | 1055 (746–1510)* |
| Salcatonin I.U./ml (HPLC) | 1068 | 1043 | 1025 | 1055 | 991 | 933 |
| Related substances | Individual < 1% | Individual < 1% | Individual < 1% | Individual < 1% | Individual < 1% | Individual < 1% |
| Sterility | Sterile | N.D. | Sterile | N.D. | Sterile | N.D. |

*Confidence limits for error (P = 0.05)
N.D. = NOT DETERMINED

TABLE 3

Salcatonin stability - Batch 961100

| Tests | 0 Time | 3 Months | 6 Months | 9 Months | 12 Months | 18 Months |
|---|---|---|---|---|---|---|
| Appearance | Corresponds | Corresponds | Corresponds | Corresponds | Corresponds | Corresponds |
| Clarity | Corresponds | Corresponds | Corresponds | Corresponds | Corresponds | Corresponds |
| Degree of coloration | Corresponds | Corresponds | Corresponds | Corresponds | Corresponds | Corresponds |
| pH | 4.03 | 4.05 | 4.07 | 3.99 | 4.10 | 4.19 |
| Salcatonin I.U./ml (biol.) | 1020 | 1040 | 1060 | 1060 | 1050 | 1048 |

TABLE 3-continued

Salcatonin stability - Batch 961100

| Tests | 0 Time | 3 Months | 6 Months | 9 Months | 12 Months | 18 Months |
|---|---|---|---|---|---|---|
|  | (1000–1336)* | (894–1310)* | (901–1431)* | (920–1399)* | (947–1292)* | (909–1331)* |
| Salcatonin I.U./ml (HPLC) | 1067 | 1017 | 1013 | 983 | 961 | 941 |
| Related substances | Individual < 1% | Individual < 1% | Individual < 1% | Individual < 1% | Individual < 1% | Individual < 1% |
| Sterility | Sterile | N.D. | Sterile | N.D. | Sterile | N.D. |

*Confidence limits for error (P = 0.05)
N.D. = NOT DETERMINED

TABLE 4

Salcatonin stability - Batch 96110

| Tests | 0 Time | 3 Months | 6 Months | 9 Months | 12 Months | 18 Months |
|---|---|---|---|---|---|---|
| Appearance | Corresponds | Corresponds | Corresponds | Corresponds | Corresponds | Corresponds |
| Clarity | Corresponds | Corresponds | Corresponds | Corresponds | Corresponds | Corresponds |
| Degree of coloration | Corresponds | Corresponds | Corresponds | Corresponds | Corresponds | Corresponds |
| pH | 4.07 | 4.11 | 4.06 | 4.05 | 4.13 | 4.24 |
| Salcatonin I.U./ml (biol.) | 2360 | 2060 | 2120 | 2080 | 2086 | 2076 |
|  | (2218–3516)* | (1792–2513)* | (1780–2862)* | (1830–2595)* | (1602–3046)* | (1716–2422)* |
| Salcatonin I.U./ml (HPLC) | 1956 | 1913 | 1860 | 1868 | 1888 | 1821 |
| Related substances | Individual < 1% | Individual < 1% | Individual < 1% | Individual < 1% | Individual < 1% | Individual < 1% |
| Sterility | Sterile | N.D. | Sterile | N.D. | Sterile | N.D. |

*Confidence limits for error (P = 0.05)
N.D. = NOT DETERMINED

TABLE 5

Salcatonin stability - Batch 961120

| Tests | 0 Time | 3 Months | 6 Months | 9 Months | 12 Months | 18 Months |
|---|---|---|---|---|---|---|
| Appearance | Corresponds | Corresponds | Corresponds | Corresponds | Corresponds | Corresponds |
| Clarity | Corresponds | Corresponds | Corresponds | Corresponds | Corresponds | Corresponds |
| Degree of coloration | Corresponds | Corresponds | Corresponds | Corresponds | Corresponds | Corresponds |
| pH | 4.06 | N.D. | 4.06 | 4.05 | 4.12 | 4.18 |
| Salcatonin I.U./ml (biol.) | 2060 | 2180 | 2120 | 2074 | 2068 | 2078 |
|  | (1978–2905)* | (1962–2856)* | (1908–2650)* | (1653–2800)* | (1656–2771)* | (1816–2574)* |
| Salcatonin I.U./ml (HPLC) | 2079 | 2052 | 2024 | 2056 | 1943 | 1799 |
| Related substances | Individual < 1% | Individual < 1% | Individual < 1% | Individual < 1% | Individual < 1% | Individual < 1% |
| Sterility | Sterile | N.D. | Sterile | N.D. | Sterile | N.D. |

*Confidence limits for error (P = 0.05)
N.D. = NOT DETERMINED

TABLE 6

Salcatonin stability - Batch 961130

| Tests | 0 Time | 3 Months | 6 Months | 9 Months | 12 Months | 18 Months |
|---|---|---|---|---|---|---|
| Appearance | Corresponds | Corresponds | Corresponds | Corresponds | Corresponds | Corresponds |
| Clarity | Corresponds | Corresponds | Corresponds | Corresponds | Corresponds | Corresponds |
| Degree of coloration | Corresponds | Corresponds | Corresponds | Corresponds | Corresponds | Corresponds |
| pH | 4.04 | 4.08 | 4.09 | 4.05 | 4.12 | 4.18 |
| Salcatonin I.U./ml (biol.) | 2320 | 2220 | 2160 | 2058 | 2182 | 2130 |
|  | (2274–3202)* | (2131–2886)* | (1879–2938)* | (1749–2572)* | (1632–2313)* | (2001–2578)* |
| Salcatonin I.U./ml (HPLC) | 1983 | 2048 | 2009 | 2047 | 1921 | 2028 |
| Related substances | Individual < 1% | Individual < 1% | Individual < 1% | Individual < 1% | Individual < 1% | Individual < 1% |
| Sterility | Sterile | N.D. | Sterile | N.D. | Sterile | N.D. |

*Confidence limits for error (P = 0.05)
N.D. = NOT DETERMINED

What is claimed is:

1. A pharmaceutical composition for intranasal administration containing in a spray dosing feeder a therapeutically effective amounts of calcitonin dissolved in a substantially physiological solution of sodium chloride in purified water, adjusted to a pH between 3.5 and 4.5 by means of citrate buffer and hydrochloric acid, wherein the citrate buffer consists of a mixture made from 0.40 to 0.70 g of citric acid monohydrate and from 0.40 to 0.70 g of sodium citrate dihydrate for each liter of solution and the pH of the solution is adjusted to a value between 3.5 and 4.5 by adding an amount of 1 N aqueous solution of hydrochloric acid between 0.08 g and 0.25 g for each liter of solution.

2. A pharmaceutical compositions according to claim 1 characterized in that the therapeutically effective amounts of calcitonin are between 500 and 2500 I.U. for each ml of solution.

3. A pharmaceutical compositions according to claim 1 characterized in that the calcitonin is the salmon calcitonin (salcatonin).

4. A pharmaceutical composition according to claim 1, wherein the spray dosing feeder is made with a bottle containing the solution of calcitonin and nitrogen under a pressure between 0.2 and 0.3 bar, and the mouth of the bottle is fitted with a dosing pump without valve of suction and delivery and is equipped with a collar packing tightly fitting the mouth of the bottle and providing a hermetic seal preventing any exchange of gas with the outside.

* * * * *